United States Patent [19]
Bergeron, Jr.

[11] Patent Number: 5,493,053
[45] Date of Patent: Feb. 20, 1996

[54] METHOD FOR PREPARING DESFERRIOXAMINE B AND HOMOLOGS THEREOF

[75] Inventor: Raymond J. Bergeron, Jr., Gainesville, Fla.

[73] Assignee: University of Florida Research Foundation, Inc., Gainesville, Fla.

[21] Appl. No.: 361,333

[22] Filed: Dec. 21, 1994

[51] Int. Cl.$^6$ ............................................. C07C 259/06
[52] U.S. Cl. .................... 562/623; 560/312; 558/390; 558/391; 558/394; 558/446; 558/451; 558/452; 524/153; 564/153
[58] Field of Search ........................... 562/623; 560/312; 564/153

[56] References Cited

U.S. PATENT DOCUMENTS

| | | | |
|---|---|---|---|
| 4,671,901 | 6/1987 | Green | 260/404.5 |
| 4,954,634 | 9/1990 | Heinrich et al. | 548/341 |
| 4,987,253 | 1/1991 | Bergeron | 562/623 |
| 5,254,724 | 10/1993 | Bergeron | 560/312 |
| 5,322,961 | 6/1994 | Bergeron | 562/623 |
| 5,367,113 | 11/1994 | Bergeron | 562/623 |

OTHER PUBLICATIONS

Katoh, A et al J. Chem Soc., Perkin Trans 1 (1991) (8) 1839–42.
Desaraju, P et al, J. Coord. Chem (1986) 14(3) 241–8.

*Primary Examiner*—Paul J. Killos
*Attorney, Agent, or Firm*—Kerkam, Stowell, Kondracki & Clarke; Dennis P. Clarke

[57] ABSTRACT

A new and versatile route to N'-[5-[[4-[[5-(acetylhydroxyamino)pentyl] amino]-1,4-dioxobutyl]hydroxyamino] pentyl] -N-(5-aminopentyl)-N-hydroxybutanediamide, desferrioxamine B (DFO) is described. N-Benzyloxy-1,5-diaminopentane is selectively protected at the primary amino site. The product is reacted at the benzyloxyamine with an anhydride to produce a carboxylic acid which is, in turn, acylated regio-specifically with a diamine at the primary amine to give a benzyloxyamine. The previous two steps are repeated to afford a DFO reagent. Acetylation of the DFO reagent, followed by hydrogenolysis and tert-butoxycarbonyl group removal, furnishes DFO.

6 Claims, 4 Drawing Sheets

FIG. 1

WEST                                                                 EAST

DFO            R = R' = H, R" = Me
DFO D₁         R = Ac, R' = H, R" = Me
DFO G          R = R' = H, R" = (CH₂)₂CO₂H
1              R = H, R' = CH₂Ph, R" = (CH₂)₂CO₂H

DFO E (Nocardamine)

Figure 4:
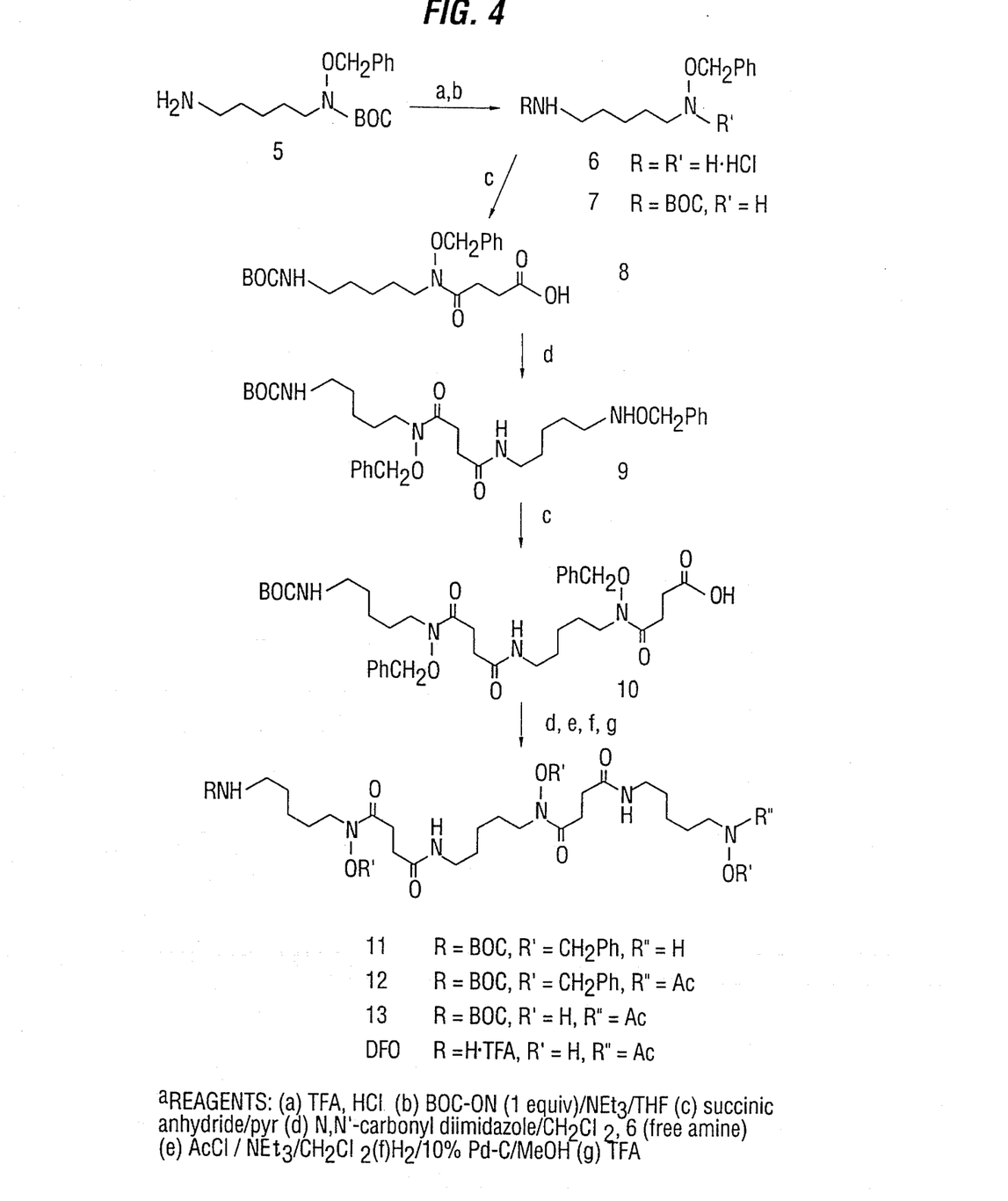
FIG. 4 depicts a typical reaction scheme for a method of the invention for producing DFO.

FIG. 4 aREAGENTS: (a) TFA, HCl (b) BOC-ON (1 equiv)/NEt₃/THF (c) succinic anhydride/pyr (d) N,N'-carbonyl diimidazole/CH₂Cl₂, 6 (free amine) (e) AcCl / NEt₃/CH₂Cl₂ (f) H₂/10% Pd-C/MeOH (g) TFA

METHOD FOR PREPARING DESFERRIOXAMINE B AND HOMOLOGS THEREOF

Support for the research which led to the present invention was provided, in part, by the National Institutes of Health (NIH) Grant No. RO1 HL-42817.

RELATED APPLICATIONS

This application contains subject matter related to that described and claimed in U.S. Pat. Nos. 4,987,253; 5,322,961 and 5,254,724, the entire contents of all of which are incorporated herein by reference.

BACKGROUND OF THE INVENTION

1. Field of the Invention

The present invention relates to an improved method for synthesizing desferrioxamine B and homologs thereof.

2. Description of the Prior Art

The microbial iron chelator, siderophore, desferrioxamine B [N'-[5-[4-[[5-acetylhydroxyamino)pentyl]amino-1,4-dioxobutyl] hydroxyamino]pentyl]-N-(5-aminopentyl)-N-hydroxybutane diamide] was isolated from *Streptomyces pilosus* and characterized by Bickel ["Metabolic products of actinomycetes. Ferrioxamine B," *Helv. Chim. Acta.*, Vol 43, pp 2129–2138] in 1960. It is a linear trihydroxamate ligand which forms a very stable hexacoordinate, octahedral [Modell et al, "The Clinical Approach to Thalassaemia," Grune and Stratton, London, pp. 217–241 (1984)] complex with Fe (III), $K_f=1\times10^{30}$ $M^{-1}$. The ligand employs its three bidentate hydroxamate units in chelating metal ions.

Although desferrioxamine B will bind a number of different +cations, e.g., Al (III), Ga (III), Cr (III), it exhibits a high specificity for Fe (III), and is utilized by *Streptomyces pilosus* for the acquisition of iron from the environment. Because of the metal selectivity and low toxicity of the ligand, it has been employed in the treatment of several iron overload diseases, e.g., thalassaemia ["Development of Iron Chelators for Clinical Use," Martell et al, eds., Elsevier, North Holland; New York (1981)]. However, desferrioxamine B does not offer a completely satisfactory solution to the iron overload problem. The drug is cleared by the kidneys and has a very short half-life in the body; thus, the patient must be maintained on constant infusion therapy. It is not orally effective. Because of these shortcomings, investigators have explored the potential of other ligands as therapeutic iron chelators. To date, these investigations have not included modification of the desferrioxamine molecule simply because of the lack of high yield of facile approaches to the synthesis of the molecule.

Desferrioxamine B was first synthesized in 1962 by Prelog et al ["Metabolic products of actinomycetes. Synthesis of Ferrioxamines B and D," *Helv. Chim Acta.*, Vol 45, pp. 631–637 (1962)]. However, because of the number of steps in the synthesis and the low yield of the sequence, the method does not enable the production of large quantities of the chelator or its analogs. A retro-synthetic analysis of the ligand reveals that the desferrioxamine molecule is made up of two fundamental units: 1-amino-5-(N-hydroxyamino-)pentane and succinic acid. The key to its synthesis is the production of this amino-hydroxyaminopentane unit and its condensation with succinic acid. Prelog approached this problem beginning with the starting material 1-amino-5-nitropentane, an amine which was accessible in only 46% yield [Bickel et al, "Metabolic products of actinomycetes. Isolation and synthesis of 1-amino-5-(hydroxyamino)pentane, an essential hydrolysis product of ferrioxamine and ferrimycin," *Helv. Chim. Acta.*, Vol. 43, pp. 901–904 (1960)]. This compound was next N-carbobenzoxylated and the terminal nitro group reduced to the corresponding hydroxyamino group. This key intermediate was condensed with succinic acid followed by a series of other dicyclohexylcarbodiimide catalyzed acylations along with several reductions to produce desferrioxamine B. The overall yield of this eleven-step sequence was 6%.

Although desferrioxamine is currently the drug of choice in the treatment of thalassemia, it nevertheless suffers from several shortcomings. The drug is not orally effective and, therefore, must be administered by infusion. Furthermore, because of its short half-life in the body, patients must be maintained on continuous infusion therapy for extended periods of time. As a result, patient compliance is the principal difficulty associated with the drug. In order to overcome these problems, investigators have explored the therapeutic potential of alternative iron chelators over the years, albeit with somewhat limited success. It was an object of the search that led to the present invention to identify methods which would allow for access to desferrioxamine itself and potentially more effective analogues and homologues. In addition, it was the intention to design a facile synthetic approach to desferrioxamine which would produce a compound that would have no possibility of contamination with proteinaceous materials associated with fermentation methods of preparation.

Bergeron et al ["An Efficient Total Synthesis of Desferrioxamine B," *J. Org. Chem.*, Vol. 53, pp. 3131–3134 (1988)] reported a total synthesis of DFO in which the construction moved from the N-acetyl to the primary amine end of the molecule.

U.S. Pat. Nos. 4,987,253 and 5,254,724 each disclose novel syntheses for desferrioxamine B and analogs and homologs thereof. U.S. Pat. No. 5,322,961 discloses novel analogs of desferrioxamine B and methods for the preparation thereof.

It is an object of the present invention to provide novel, improved, high yield methods for the production of desferrioxamine B and homologs thereof.

SUMMARY OF THE INVENTION

The above and other objects are realized by the present invention, one embodiment of which relates to a method for synthesizing desferrioxamine B or a homolog thereof having the formula:

$$H_2N(CH_2)_{n+1}N\underset{|}{\overset{OH}{\phantom{N}}}CO(CH_2)_aCONH(CH_2)_{n+1}- \quad (1)$$

wherein:

each n may be the same or different and is an integer from 1 to 10;

a and b may be the same or different and are integers from 1 to 6; and

R is an alkyl group having from 1 to 10 carbon atoms or an aryl group, comprising:

(a) condensing a diamine having the formula:

$$\text{QNH(CH}_2)_n\text{NH} \quad \overset{\text{OZ}}{|} \tag{7}$$

wherein Z is a hydroxyl protecting group and Q is an amino protecting group, with an anhydride having the formula:

to produce a carboxylic acid having the formula:

wherein n is an integer from 2 to 10,

(b) condensing the carboxylic acid (8) with an amine having the formula:

$$\text{NH}_2(\text{CH}_2)_n\text{NH} \quad \overset{\text{OZ}}{|} \tag{6}$$

to produce an amide having the formula:

$$\overset{\text{OZ}}{|}\qquad\overset{\text{OZ}}{|} \tag{9}$$
$$\text{QNH(CH}_2)_n\text{N—CO(CH}_2)_a\text{CONH(CH}_2)_n\text{NH}$$

(c) condensing amide (9) with an anhydride having the formula:

to produce a carboxylic acid having the formula:

$$\overset{\text{OZ}}{|}\qquad\overset{\text{OZ}}{|} \tag{10}$$
$$\text{QNH(CH}_2)_n\text{NCO(CH}_2)_a\text{CONH(CH}_2)_n\text{NCO(CH}_2)_b\text{COOH}$$

(d) condensing compound (10) with amine (6) to produce an amide having the formula:

$$\overset{\text{OZ}}{|} \tag{11}$$
$$\text{QNH(CH}_2)_n\text{NCO(CH}_2)_a\text{CONH(CH}_2)_n\text{—}$$

$$\overset{\text{OZ}}{|}\qquad\overset{\text{OZ}}{|}$$
$$\text{—NCO(CH}_2)_b\text{CONH(CH}_2)_n\text{NH}$$

(e) acylating amide (11) to produce a compound having the formula:

$$\overset{\text{OZ}}{|} \tag{12}$$
$$\text{QNH(CH}_2)_n\text{NCO(CH}_2)_a\text{CONH(CH}_2)_n\text{—}$$

$$\overset{\text{OZ}}{|}\qquad\overset{\text{OZ}}{|}$$
$$\text{—NCO(CH}_2)_b\text{CONH(CH}_2)_n\text{N—COR}$$

(f) cleaving Z from compound (12) to produce a compound having the formula:

$$\overset{\text{OH}}{|} \tag{13}$$
$$\text{QNH(CH}_2)_n\text{NCO(CH}_2)_a\text{CONH(CH}_2)_n\text{—}$$

$$\overset{\text{OH}}{|}\qquad\overset{\text{OH}}{|}$$
$$\text{—NCO(CH}_2)_b\text{CONH(CH}_2)_n\text{N—COR}$$

(g) cleaving Q from compound (13) to produce the compound of formula (1).

DETAILED DESCRIPTION OF THE INVENTION

Microorganisms produce a group of low molecular weight chelators, siderophores [Bergeron, "Synthesis and Solution Structures of Microbial Siderophores," *Chem. Rev.*, Vol. 84, pp. 587–602 (1984); Tait, "The Identification and Biosynthesis of Siderochromes Formed by *Micrococcus denitrificans, Biochem. J.*, Vol. 146, pp. 191–204 (1975); Griffiths et al, "Vibriobactin, a Siderophore from *Vibrio cholerae,*" *J. Biol. Chem.*, Vol. 259, pp. 383–385 (1984); Aksoy et al, "Hypertransfusion and Iron Chelation in Thalassaemia," p. 80, Hans Huber Publishers, Berne (1985); and Bickel et al, "Metabolic products of actinomycetes. Ferrioxamine B," *Helv. Chim. Acta.*, Vol. 43, pp. 2129–2138 (1960)] for the purpose of acquiring iron. The metal exists in the biosphere largely in the insoluble ferric state and would be otherwise inaccessible to bacteria without such ligands. Although a large number of siderophores have been identified, they fall largely into two structural classes: the catecholamides and the hydroxamates [Bergeron, supra]. Many of the ligands of both structural types contain polyamine backbones. While the hexacoordinate catecholamides parabactin [Tait, supra] and vibriobactin [Griffiths et al, supra] are predicated on the triamines spermidine and norspermidine, respectively, the hydroxamates are frequently derived from the diamines, putrescine or cadaverine, or from their biochemical precursors, ornithine or lysine [Bergeron, supra]. For example, the siderophores isolated from *Streptomyces pilosus*, desferrioxamines A-I, consist of a group of hydroxamates with either repeating putrescine or cadaverine units in their backbones [Aksoy et al, supra]. The most well known of these chelators, desferrioxamine B (DFO) [Bickel et al, supra], is a linear trihydroxamate ligand which forms a very stable hexacoordinate, octahedral complex [Modell et al, "The Clinical Approach to Thalassaemia," p. 217, Grune and Stratton, London (1984)] with iron (III), $K_f=1\times10^{30}$ $M^{-1}$. Although DFO binds a number of different +cations, e.g., Al (III), Ga (III), Cr (III), it exhibits a high specificity for iron (III). It is not too surprising then that the mesylate salt of desferrioxamine, Desferal®, has been employed in the treatment of several iron overload diseases such as thalassemia [Anderson, "Inorganic Chemistry in Biology and Medicine," Chapter 15, American Chemical Society, Washington, D.C. (1973); and Fisher et al, "Development of an Intravenous Desferrioxamine Mesylate Treatment Protocol for Swine: Monitoring of Desferrioxamine and Metabolites By High-Performance Liquid Chromatography," *Pharmacology*, Vol. 41, pp. 263–271 (1990)]. However, the fact that patients must be continuously infused because of the short half-life of the drug in the body has compelled investigators to continue the search for better therapeutic iron chelators.

Figure 1:
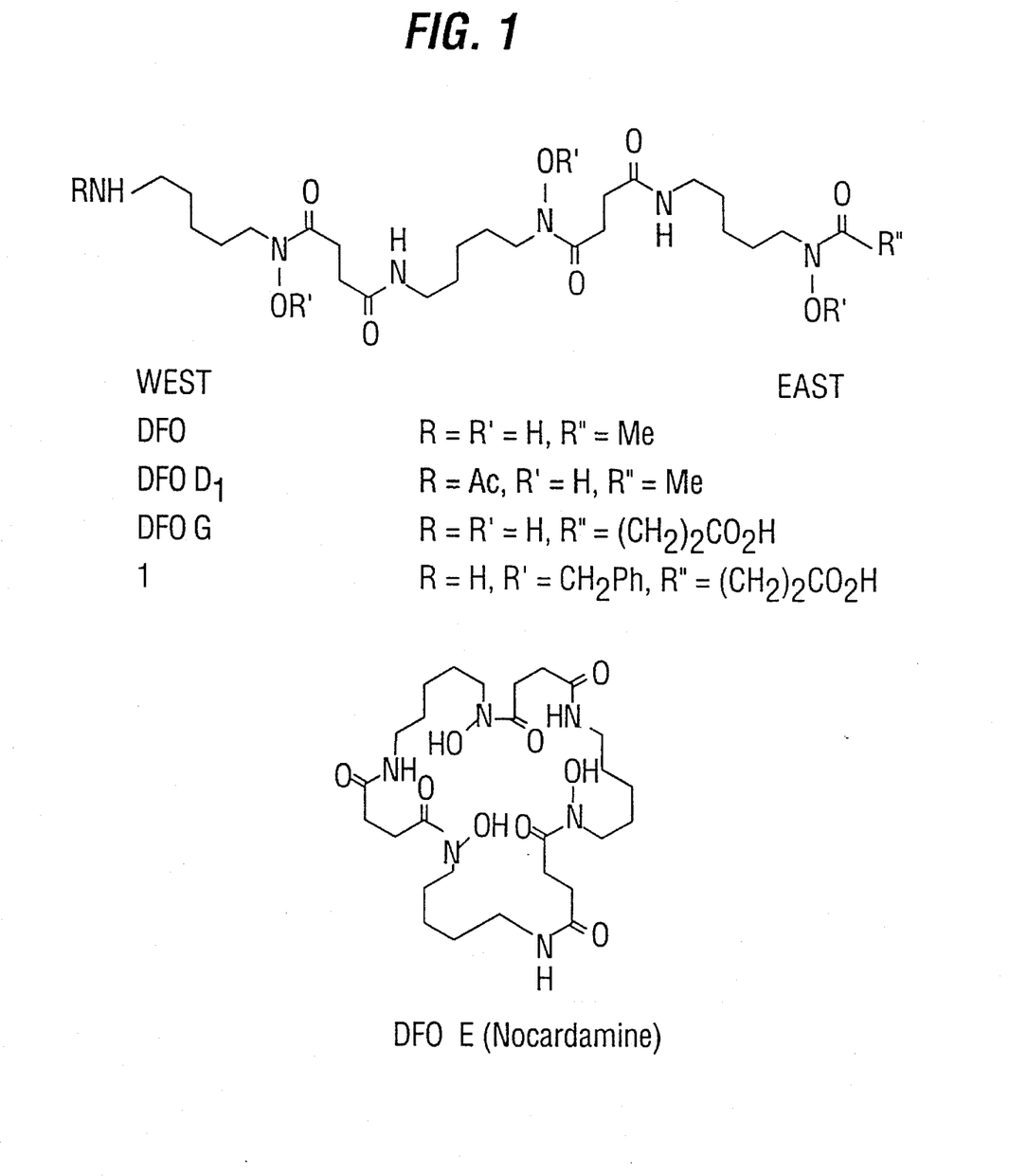
FIG. 1 depicts the structural formulae of DFO and analogs thereof.

Two syntheses of DFO are set forth in U.S. Pat. Nos. 4,987,253 and 5,254,724. Both of these methodologies focussed on the key intermediate (2) (FIG. 2) in which the three hydroxamates are protected by benzyls and the primary amine is masked as a nitrile. The first synthesis of DFO described in U.S. Pat. No. 4,987,253 began with the somewhat tedious production of 4-cyanobutanal, a moderately unstable aldehyde. The synthesis of (2) then moved from the N-acetyl to the primary amino end of the molecule, or east to west (FIG. 1).

Figure 2:
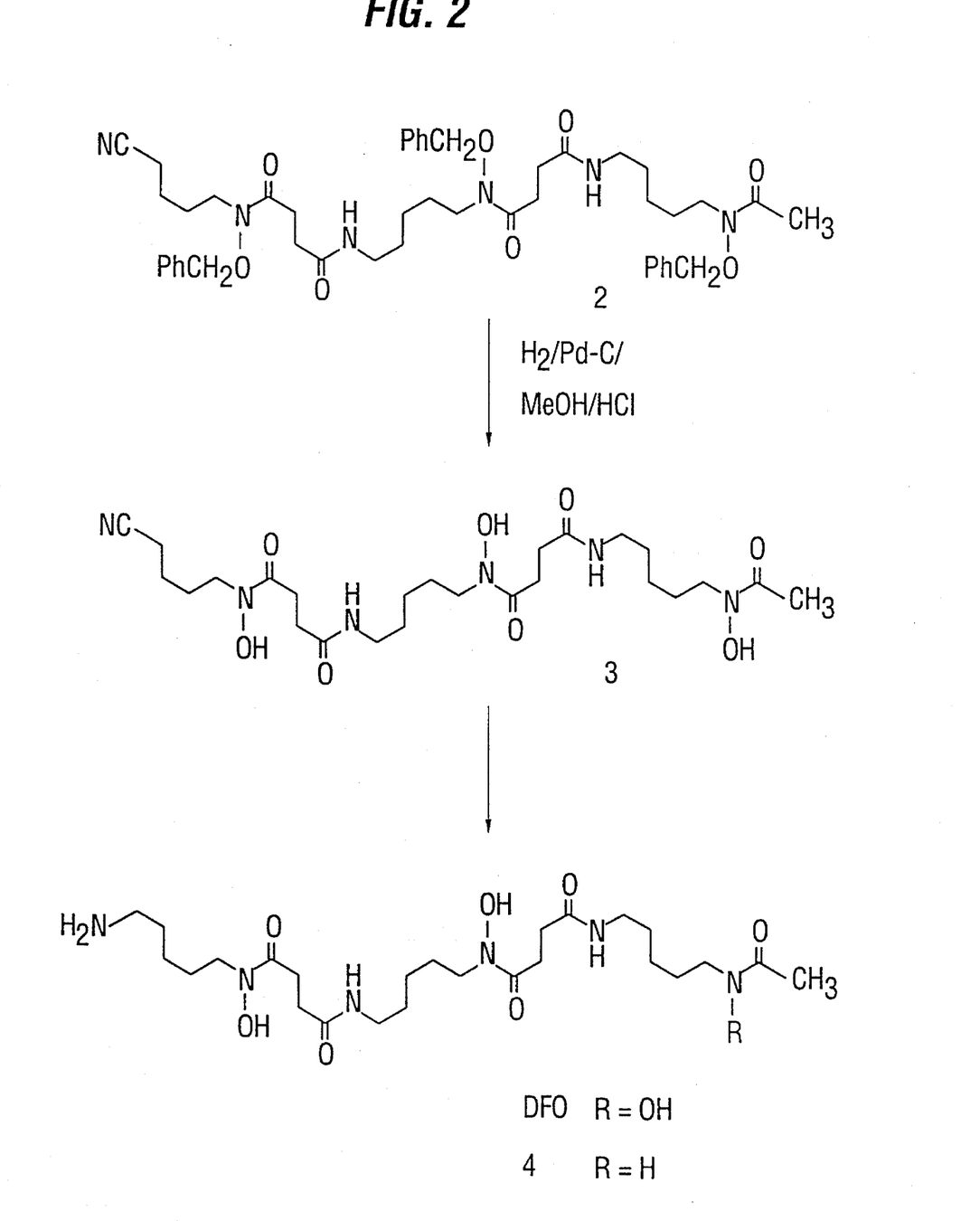
FIG. 2 depicts a partial reaction scheme for the methods of the prior art for producing DFO.
Figure 3:
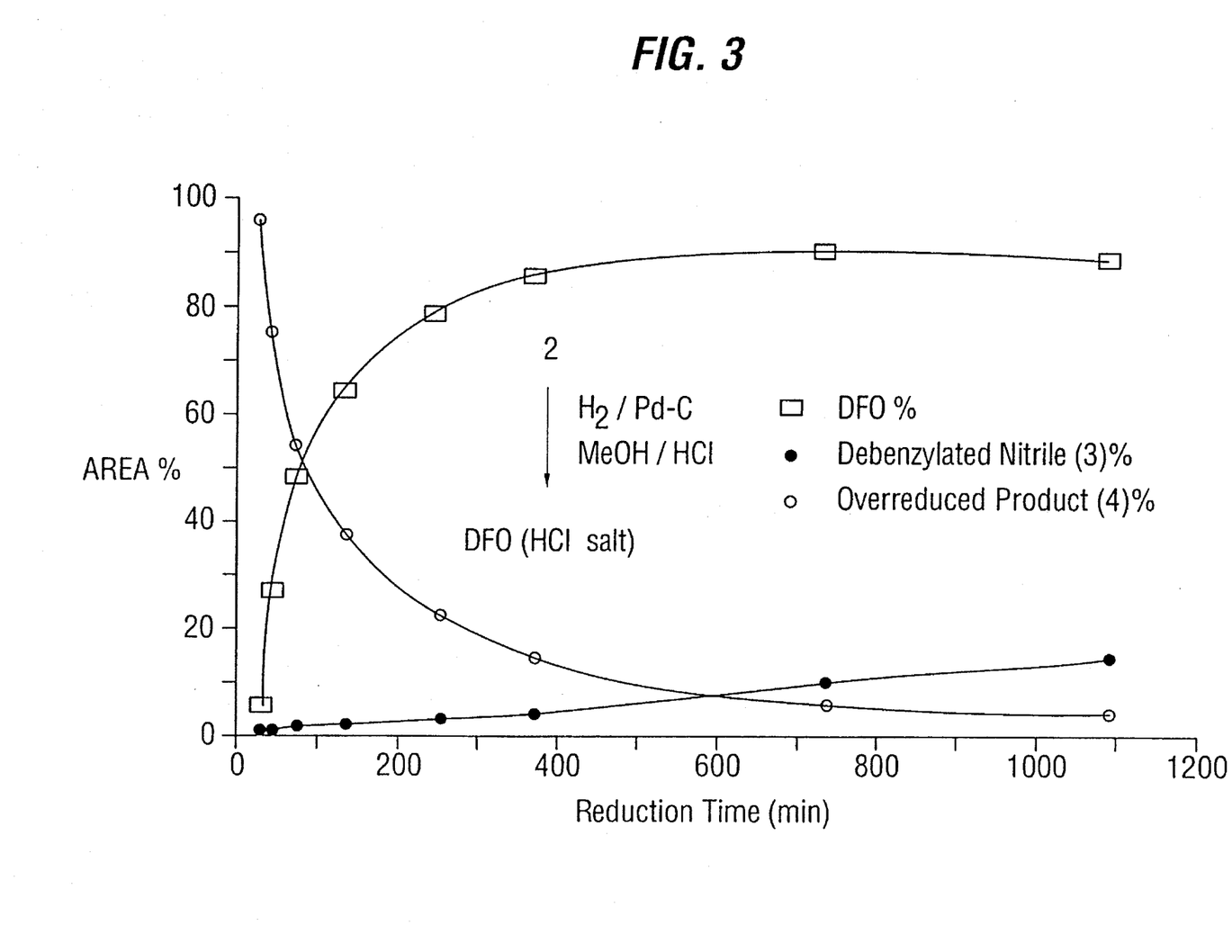
FIG. 3 depicts nitrile reduction versus hydroxamate over-reduction during reduction of intermediates to DFO in methods of the prior art.

The second scheme described in U.S. Pat. No. 5,254,724 began with N-(tert-butoxycarbonyl)-O-benzylhydroxylamine, which is crystalline, stable and available in a single step from commercial reagents. N-Alkylation with 5-chlorovaleronitrile (NaH, DMF, NaI) gave O-benzyl-N-tert-butoxycarbonyl)-N-( 4-cyanobutyl)hydroxylamine, a tri-protected N-hydroxy-1,5-pentanediamine reagent, which was elaborated to the DFO precursor (2) in the opposite direction, that is, west to east (FIG. 2). Because the acetyl terminus was not attached until near the end of the synthesis, this route was more suitable for the production of DFO analogs containing other acyl groups.

In both DFO preparations, the catalytic hydrogenation of (2) (e.g., 10% Pd-C, MeOH, HCl, 1 atm) simultaneously cleaved the benzyl protecting groups and saturated the nitrile to a primary amine to furnish DFO. While the benzyl moieties were cleaved in less than one-half hour, resulting in under-reduced intermediate (3) (FIG. 2), the cyano function required longer times for saturation. Prolonged reduction times generated not only DFO, but a troublesome product of over-reduction, the acetamide (4) (FIG. 2). The kinetics of reduction could be followed by HPLC and by $^1$H NMR in that the acetamide peak ($\delta$ 1.96) of (4) was upfield from the acetyl signal of DFO ($\delta$ 2.14). Based on these studies, 4 hours was found to be the optimum time for exposure to hydrogen. Nevertheless, it was still necessary to remove over-reduced product (4).

The method of the present invention represents an improvement over both of the earlier patented methods. The present new route not only contains the advantages of the second synthesis (i.e., that of U.S. Pat. No. 5,254,724), but also (1) eliminates the problems associated with nitrile reduction by replacing the western terminus of (2) with a tert-butoxycarbonyl (BOC)-protected amine, (2) streamlines the building of the DFO chain by capitalizing on the electronic differences between a primary amine and an O-benzyloxyamine and (3) allows for the convenient modification of either terminus of the chelator.

As in the second route, the backbone of DFO was constructed by a series of acylations such that the acetyl function was attached at the end of the synthesis, that is, west to east. Construction of the siderophore began with N-benzyloxy-N-(tert-butoxycarbonyl)-1,5-pentanediamine (5) (FIG. 4) which was obtained from Raney nickel hydrogenation of the nitrile of the tri-protected N-hydroxy-cadaverine reagent [Bergeron et al, Tetrahedron, Vol. 45, pp. 4939–4944 (1989)]. Unlike the nickel-catalyzed hydrogenation of the first route, no special precautions were needed to prevent base-promoted side reactions. Exposure of (5) to, e.g., trifluoroacetic acid (TFA) and then HCl provided N-benzyloxy-1,5-pentanediamine dihydrochloride (6) which is also available by alkylation of O-benzylhydroxylamine with N-(5-bromopentyl)phthalimide, followed by hydrazinolysis [Kolasa et al, *Pol. J. Chem.*, Vol. 55, pp. 1163–1167, (1981)].

Replacement of the nitrile of (2) with a BOC-protected amine could be readily achieved if diamine (6) could be selectively functionalized using a BOC reagent at the primary amine. N-Benzyloxy-1,5-diaminopentane (6) as its free amine was treated with 2-(tert-butoxycarbonyloxy-imino)-2-phenylacetonitrile (BOC-ON, 1 equiv) in THF at 0° C., cleanly providing N-benzyloxy-N'-tert-butoxycarbonyl)-1,5-pentanediamine (7). Both steric [Cohen et al, *J. Chem. Soc., Chem. Commun.*, pp. 298–300 (1992)] and electronic [Frenna et al, *J. Chem. Soc., Perkin Trans. II*, pp. 1865–1868 (1985) and Mollin et al, *Chem. Zvesti*, Vol. 29, pp. 39–43 (1975)] factors explain the high regioselectivity of this transformation.

Benzyloxyamine (7) was heated with succinic anhydride in pyridine, giving carboxylic acid (8). Thus, this route to DFO is even more streamlined than before in that the benzyloxyamine nitrogen need not be de-protected before addition to succinic anhydride. Treatment of acid (8) with 1,1'-carbonyldiimidazole (CDI) [Chemical Abstracts, Vol. 111, No. 78599g (1989) as it relates to Peter et al, European Patent Application No. EP 300,966 (1989)] in $CH_2Cl_2$ generated the N-acyl imidazole in situ, and a solution of (6) as the free diamine in $CH_2Cl_2$ was slowly added at 0° C., resulting in N-benzyloxyamine (9). CDI was an especially convenient amide-forming reagent in that the imidazole by-product was washed out during work-up. As was the case in the protection of diamine (6) by BOC, acylation occurred at the primary amine end of (6) with a high degree of selectivity [Joshua et al, *Tetrahedron Lett.*, Vol. 25, pp. 5725–5728 (1984); Milewska et al, *J. Prakt. Chem.*, Vol. 329, pp. 447–456 (1987); and Lee et al, *J. Org. Chem.*, Vol. 48, pp. 24–31 (1983)].

The last two steps were repeated to generate DFO reagent (11). That is, N-benzyloxyamine (9) was converted to acid (10) with succinic anhydride in pyridine. Next, regio-specific acylation of diamine (6) with acid (10) gave tris(N-benzyloxyamine) (11). In addition to providing DFO in three transformations, (11) is a versatile DFO reagent in which the eastern end of DFO can be modified with a wide range of acylating agents. For example, radiolabeled DFO could be made by coupling with $^3$H- or $^{14}$C-acetic acid (11).

Reaction of (11) with acetyl chloride ($NEt_3/CH_2Cl_2$) produced fully protected DFO (12). The benzyl groups of (12) were cleaved by hydrogen under mild conditions (10% Pd-C/$CH_3OH$, 1 atm, room temperature) within 20 minutes to give N-(tert-butoxycarbonyl)DFO (13) which was identical by a high field $^1$H NMR spectrum to an authentic sample. Thus, catalytic unmasking of the hydroxamate esters of (12) with no special precautions was completed in 20 minutes with no detectable nitrogen-oxygen bond cleavage. This result can be compared to the last step of the first two routes using FIG. 1, that is, hydrogenation of tris(N-benzyloxy)nitrile (2). Since the benzyl groups were cleaved faster than the nitrile was saturated, the molecule was greater than 90% in the form of the intermediate trihydroxynitrile (3) after 20 minutes. Most of the cyano function was saturated as well after 4 hours, resulting in DFO (77%) along with intermediate (3) (21%) and over-reduced product (4) (2%). After 12 hours, DFO (88%) was accompanied by only 4% of nitrile (3), but 8% of over-reduced product (4).

Brief exposure of N-(tert-butoxycarbonyl) DFO (13) to trifluoroacetic acid (TFA) at 0°–5° C. for 20 minutes resulted in the formation of DFO (1) as its trifluoroacetate salt, along with isobutylene and carbon dioxide.

Thus, replacement of the nitrile of (2) with a terminal amine, protected by BOC, already in place from the beginning of the synthesis, increased the overall efficiency of the DFO preparation. Also, the order of the last two steps of this synthesis (FIG. 4) is not important. Moreover, if the last step were carried out with methanesulfonic acid in dioxane [Kiso et al, *Int. J. Pept. Protein Res.*, Vol. 40, pp. 308–314 (1992)], Desferal® could be accessed directly.

Using this methodology, additional hydroxamate siderophores and analogs could be prepared more efficiently than by any other published route. As mentioned before, the sequence of acylation of DFO synthon (11) can provide a variety of DFO analogs. These would be valuable for determining structure-activity relationships in the search for chelators with a longer clearance time and perhaps oral viability. Also other siderophores from *Streptomyces pilosus* could be synthesized more efficiently than before. For example, BOC-benzyloxyamine (11) could be heated with succinic anhydride (pyr) and then stirred with TFA to give ω-amino acid (1) (FIG. 2) which is the acyclic precursor to macrocyclic DFO E (nocardamine). In that route, (1) was prepared from the corresponding ω-cyano carboxylic acid by hydrogenation (Raney nickel) in only 21% yield due to cleavage of the chain by alkaline reaction conditions. Hydrogenation of (1) under mild conditions (10% Pd-C/ $CH_3OH$/20 minutes) would give DFO G, a trihydroxamate ω-amino acid (FIG. 2). If DFO reagent (11) were reacted with TFA, both termini of the resulting ω-amino N-benzyloxyamine could be derivatized with the same acyl group. For example, subsequent treatment of the diamine with acetyl chloride (2 equiv, $NEt_3CH_2Cl_2$) and then hydrogenolysis of the benzyl protecting groups would generate the neutral DFO, $D_1$.

The invention is illustrated by the following non-limiting examples, wherein silica was used for column chromatography; proton NMR spectra were run at 90 or 300 MHz in $CDCl_3$ (not indicated) or $D_2O$ with chemical shifts given in parts per million downfield from tetramethylsilane or 3-(trimethylsilyl)propionic- 2,2,3,3-$d_4$ acid, sodium salt, respectively; coupling constants (J) are in hertz; and variable temperature NMR studies were run at 600 MHz.

EXAMPLE 1

N-Benzyloxy-1,5-pentanediamine dihydrochloride (6)

Trifluoroacetic acid (TFA, 30 mL) was added to a solution of (5) (19.4 g, 63.0 mmol) [Bergeron et al, *Tetrahedron*, Vol. 45, pp. 4939–4944 (1989)] in $CHCl_2$ (100 mL) at 0° C. The solution was stirred at room temperature for 30 minutes under nitrogen and excess TFA was removed by rotary evaporation. The residue was carefully basified with cold 1 N NaOH (50 mL) and then 50% NaOH (23 mL) until pH> 14 and extracted with $CHCl_3$ (3×60 mL). After solvent removal, the residue was taken up in EtOH (100 mL) and treated with concentrated HCl (12 mL) with cooling. After solvent removal, recrystallization from absolute EtOH generated 14.4 g of (6) (82%) as a white solid: mp 179°–181° C. (lit mp 170°–172° C.) [Kolasa et al, *Pol. J. Chem.*, Vol. 55, pp. 1163–1167 (1981)] NMR ($D_2O$) δ 1.3–1.9 (m, 6 H), 2.95 (t, 2 H, J=7), 3.22 (t, 2 H, J=7), 5.1 (s, 2 H), 7.45 (s, 5 H). Anal. calcd. for $C_{12}H_{22}Cl_2N_2O$: C, 51.25; H, 7.89; N. 9.96. Found: C, 51.33; H, 7.94; N, 9.90.

EXAMPLE 2

N-Benzyloxy-N'-(tert-butoxycarbonyl)-1,5-pentanediamine (7)

1 N NaOH (100 mL) was added to (6) (6.01 g, 21.4 mmol), followed by extraction with ether (5×50 mL). After a brine wash (50 mL), solvent was removed to give 4.39 g of (6) as the free amine. BOC-ON (5.10 g, 20.7 mmol) in distilled THF (100 mL) was added to (6) (free amine, 21.1 mmol) in THF (165 mL) at 0° C. over 30 minutes. The reaction was stirred (0° C. to room temperature) for 24 hours and concentrated in vacuo. Cold 1N NaOH (100 mL) was added, followed by extraction with EtOAc (4×100 mL). The organic layer was washed with cold 1 N NaOH (3×80 mL), cold 0.5M citric acid (100 mL) and brine (2×100 mL). Removal of solvent gave 6.38 g (quantitative) of (7), which was used directly in the next step, as a liquid: NMR δ 1.2–1.7 (m+ s, 15 H), 2.66–3.23 (m, 4 H), 4.5 (br s, 1 H), 4.67 (s, 2 H), 7.16–7.34 (m, 5 H). An analytical sample was purified on a silica gel column, eluting with 15% EtOAc/ $CHCl_3$. Anal. calcd. for $C_{17}H_{28}N_2O_3$: C, 66.20; H, 9.15; N, 9.08. Found: C, 66.13; H, 9.10; N, 9.05.

EXAMPLE 3

5-Benzyloxy-11-(tert-butoxycarbonyl)-4-oxo-5,11-diazaundecanoic acid (8)

Pyridine (80 mL) was added to (7) (6.38 g, 20.7 mmol) and succinic anhydride (3.11 g, 31.1 mmol) and the reaction was heated under nitrogen at 80°–86° C. for 1.5 hours. Solvent was removed under high vacuum and the residue was dissolved with ether (150 mL) and washed with saturated $NaHCO_3$ (4× 50 mL). The aqueous portion was extracted with ether (2× 50 mL), cooled to 0° C., acidified with cold 1N HCl (350 mL) and extracted with CHCl] (6×100 mL). A water wash (100 mL), solvent removal and flash column chromatography, eluting with 6% $CH_3OH$/ $CH_2Cl_2$, gave 7.46 g (88%) of (8) as a solid: mp 93°–94° C., NMR δ 1.2–1.8 (m+ s, 16 H), 2.62 (s, 4 H), 2.9–3.2 (m, 2 H), 3.51–3.76 (m, 2 H), 4.8 (s, 2 H), 7.33 (s, 6 H). Anal. calcd. for $C_{21}H_{32}N_2O_6$: C, 61.75; H, 7.90, N, 6.86. Found: C, 61.48; H, 7.90; N, 6.79.

EXAMPLE 4

7,18-Bis(benzyloxy)-1-(tert-butoxycarbonyl)-8,11-dioxo-1,7,12, 18-tetraazaoctadecane (9)

Carbonyldiimidazole (CDI, 0.592 g, 3.65 mmol) was added to (8) (1.42 g, 3.48 mmol) in dry $CH_2Cl_2$ (90 mL). After stirring for 1 hour, the solution was cooled to 0° C. and (6) (free amine, 0.74 g, 3.55 mmol) in $CH_2Cl_2$ (65 mL) was added by cannula over 5 minutes. After stirring for 12 hours (0° C. to room temperature), solvent was removed by rotary evaporation. Dilute brine (200 mL) was added, followed by extraction with EtOAc (4×100 mL). The organic phase was washed with 100 mL portions of cold 0.5M citric acid, 5% $NaHCO_3$ and brine. Solvent removal led to 2.2 g (quantitative) of (9) as an oil, which was used directly in the next step. An analytical sample was chromatographed on silica gel, eluting with 3.5% EtOH/$CHCl_3$: 300 MHz NMR δ 1.1–1.7 (m+ s, 21 H), 2.3–3.3 (m, 10 H), 3.60 (t, 2 H, J=7), 4.6 (br s, 1 H), 4.67 (s, 2 H), 4.80 (s, 2 H), 6.0 (br s, 1 H), 7.25–7.40 (m, 10 H). Anal. calcd. for $C_{33}H_{50}N_4O_6$: C, 66.19; H, 8.42; N, 9.36. Found: C, 66.27; H, 8.40; N, 9.33.

EXAMPLE 5

5,16-Bis (benzyloxy)-22-(tert-butoxycarbonyl)-4,12,15-trioxo-5,11,16,22-tetraazadocosanoic acid (10)

A mixture of (9) (2.2 g, 3.48 mmol), succinic anhydride (0.55 g, 5.5 mmol) and pyridine (70 mL) was heated at 81° C. for 2 hours. Solvent was removed in vacuo and cold 1N HCl (100 mL) was added. Extraction was carried out with $CHCl_3$ (6×75 mL), followed by a water wash (100 mL). Solvent removal and flash column chromatography, eluting with 7% $MeOH/CH_2Cl_2$, afforded 1.98 g (81%) of (10) as an oil: 300 MHz NMR δ 1.2–1.7 (m+ s, 21 H), 2.53 (t, 2 H, J=7), 2.67 (s, 4 H), 2.78–2.86 (m, 2 H), 3.02–3.11 (m, 2 H), 3.22 (q, 2 H, J=6), 3.56–3.77 (m, 4 H), 4.7 (br s, 1 H), 4.83 (s, 2 H), 4.86 (s, 2 H), 6.73 (br s, 1 H), 7.38 (s, 10 H). Anal. calcd. for $C_{37}H_{54}N_4O_9$: C, 63.59; H, 7.79; N, 8.02. Found: C, 63.4 5; H, 7.81; N, 8.07.

EXAMPLE 6

1-(tert-Butoxycarbonyl) -7,18,29-tris(benzyloxy)-8,11,19,22-tetraoxo-1,7,12,18,23,29-hexaazanonacosane (11)

CDI (0.188 g, 1.16 mmol) was added to a solution of (10) (0.76 g, 1.09 mmol) in dry $CH_2Cl_2$ (45 mL). The solution was cooled to 0° C. after 1 hour and (6) (free amine, 0.240 g, 1.15 mmol) was added by cannula in $CH_2Cl_2$ (60 mL) over 5 minutes. The reaction was stirred at 0° C. to room temperature for 24 hours. Solvent was removed in vacuo and dilute brine (100 mL) was added to the residue. Extraction was carried out with EtOAc (5×75 mL), followed by washing with 50 mL of cold 0.5M citric acid, 5% $NaHCO_3$, water and brine. Solvent removal gave 0.87 g (90%) of (11) which was used directly in the next reaction: NMR δ 1.1–1.8 (m+ s, 27 H), 2.3–3.7 (m, 20 H), 4.5 (br s, 1 H), 4.67 (s, 2 H), 4.82 (s, 4 H), 6.2 (br s, 1 H), 7.2–7.4 (m, 15 H). An analytical sample of (11) was obtained from silica gel column chromatography, eluting with 5% $MeOH/CHCl_3$. Anal. calcd. for $C_{49}H_{72}N_6O_9$: C, 66.19; H, 8.16; N, 9.45. Found: C, 66.18; H, 8.17; N, 9.42.

EXAMPLE 7

1-(tert-Butoxycarbonyl)-7,18,29-tris(benzyloxy)-8,11,19,22,30-pentaoxo-1,7,12,18,23,29-hexaazahentriacontane (12)

$NEt_3$ (0.16 mL, 1.15 mmol) was added to (11) (0.87 g, 0.98 mmol) in $CH_2Cl_2$ (40 mL) and the solution was cooled to 0° C. Acetyl chloride (0.074M in $CH_2Cl_2$, 14 mL, 1.04 mmol) was added by syringe over 4 minutes and stirring was continued (0° C. to room temperature) for 24 hours. The aqueous phase was extracted with $CH_2Cl_2$ (4×50 mL) and the organic phase was washed with 40 mL portions of cold 0.25M citric acid, 5% $NaHCO_3$ and $H_2O$. Solvent removal and flash column chromatography with 60% acetone/hexane gave 0.79 g (87%) of (12) as an oil: 300 MHz NMR δ 1.23–1.69 (m+ s, 27 H), 2.09 (s, 3 H), 2.44–2.53 (m, 4 H), 2.76–2.84 (m, 6 H), 3.03–3.24 (m, 6 H), 3.57–3.68 (m, 6 H), 4.7 (br s, 1 H), 4.81 (s, 2 H), 4.85 and 4.86 (2 s, 4 H), 6.35 (br s, 1 H), 7.38 (s, 15 H). Anal. calcd. for $C_{51}H_{74}N_6O_{10}$: C, 65.78; H, 8.01; N, 9.03. Found: C, 65.89; H, 8.04; N, 8.95.

EXAMPLE 8

1-(tert-Butoxycarbonyl)-7,18,29-trihydroxy-8,11,19,22,30-pentaoxo-1,7,12,18,23,29-hexaazahentriacontane (13)

10% Pd-C (227 mg) was added to a solution of (12) (0.346 g, 0.372 mmol) in MeOH (100 mL). The reaction flask was degassed three times with nitrogen and hydrogen gas was introduced at 1 atm. The mixture was rapidly stirred at room temperature for 20 minutes. After the reaction flask was evacuated and filled with nitrogen several times, the catalyst was filtered through a sintered glass filter (10–15μ) and solids were washed with MeOH. After solvent removal by rotary evaporation, the residue was passed through a short Sephadex LH-20 column, eluting with MeOH. The band was dried to provide 199 mg (81%) of (13) as an amorphous white solid: 300 MHz NMR ($d_6$-DMSO) δ 1.12–1.53 (m+ s, 27 H), 1.95 (s, 3 H), 2.25 (t, 4 H, J=7), 2.52–2.60 (m, 4 H), 2.82–3.03 (m, 6 H), 3.43 (t, 6 H, J=6), 7.4 (m, 1 H), 7.8 (m, 2 H), 9.7 (br s, 3 H). The spectrum was identical to an authentic sample of (13).

EXAMPLE 9

Desferrioxamine B Trifluoroacetate (DFO)

Compound (13) (19.5 mg, 0.030 mmol) was cooled to 0° C. under argon. TFA (2.4 mL) was added by pipette, and the reaction was stirred at 0° C. for 20 minutes. Excess TFA was removed under high vacuum at 1°–4° C. on the rotary evaporator and then at room temperature to give 25.1 mg (quantitative) of DFO trifluoroacetate as a glass: 300 MHz ($D_2O$) δ 1.23–1.77 (m, 18 H), 2.10 and 2.12 (2 unequal s, 3 H), 2.49 (t, 4 H, J=7), 2.63–2.84 (t and br s, 4 H, J=7), 2.98 (t, 2 H, J=7), 3.15 (t, 4 H, J=7), 3.56–3.70 (m, 6 H). This spectrum was identical to Desferal®, except for the methanesulfonate singlet in the latter, and to DFO hydrochloride, obtained from passing Desferal® through a column packed with BioRad Anion Exchange Resin AG1-X8 (hydroxide form).

I claim:

1. A method for synthesizing desferrioxamine B or a homolog thereof having the formula:

wherein:

each n may be the same or different and is an integer from 1 to 10;

a and b may be the same or different and are integers from 1 to 6; and

R is an alkyl group having from 1 to 10 carbon atoms or an aryl group, comprising:

(a) condensing a diamine having the formula:

wherein Z is a hydroxyl protecting group and Q is an amino protecting group, with an anhydride having the formula:

to produce a carboxylic acid having the formula:

(8)

wherein n is an integer from 2 to 10,

(b) condensing the carboxylic acid (8) with an amine having the formula:

(6)

to produce an amide having the formula:

(9)

(c) condensing amide (9) with an anhydride having the formula:

to produce a carboxylic acid having the formula:

(10)

(d) condensing compound (10) with amine (6) to produce an amide having the formula:

(11)

$$-NCO(CH_2)_bCONH(CH_2)_nNH$$

(e) acylating amide (11) to produce a compound having the formula:

(12)

$$-NCO(CH_2)_bCONH(CH_2)_nN-COR$$

(f) cleaving Z from compound (12) to produce a compound having the formula:

(13)

(g) cleaving Q from compound (13) to produce said compound of formula (1).

2. The method of claim 1 for producing desferrioxamine B.

3. The method of claim 1 including the steps of cleaving Q from a compound of the formula:

(5)

to produce a compound of the formula:

(6)

followed by reaction of compound (6) with a primary amine protecting reagent to produce compound (7).

4. The method of claim 3 including the steps of alkylating a hydroxylamine having the formula:

$$ZONH_2$$

with an N-alkylating agent having the formula:

to produce a hydrazine having the formula:

followed by hydrazinolysis of said hydrazine to form compound (6), followed by reacting compound (6) with a primary amine protecting reagent to produce compound (7).

5. The method of claim 3 wherein said compound (5) is prepared by reduction of the compound having the formula:

(4)

6. The method of claim 5 including the step of preparing compound (4) by reacting a hydroxylamine having the formula:ps (2)

with an N-alkylating agent having the formula:

(3).

* * * * *

UNITED STATES PATENT AND TRADEMARK OFFICE
CERTIFICATE OF CORRECTION

PATENT NO. : 5,493,053
DATED : Feb. 20, 1996
INVENTOR(S) : Raymond J. BERGERON, Jr.

It is certified that error appears in the above-indentified patent and that said Letters Patent is hereby corrected as shown below:

Column 12,
Claim 6, line 3, after the word "formula," delete "ps"

Signed and Sealed this

Eighteenth Day of June, 1996

Attest:

BRUCE LEHMAN

*Attesting Officer*  *Commissioner of Patents and Trademarks*